United States Patent

Layzell et al.

[11] Patent Number: 5,542,284
[45] Date of Patent: Aug. 6, 1996

[54] METHOD AND INSTRUMENT FOR MEASURING DIFFERENTIAL OXYGEN CONCENTRATION BETWEEN TWO FLOWING GAS STREAMS

[75] Inventors: David B. Layzell; Stephen Hunt; Adrian N. Dowling, all of Kingston, Canada

[73] Assignee: Queen's University at Kingston, Kingston, Canada

[21] Appl. No.: 324,645

[22] Filed: Oct. 18, 1994

[51] Int. Cl.[6] .................................................. G01N 27/04
[52] U.S. Cl. ........................................... 73/23.2; 73/23.21
[58] Field of Search ............................ 73/16, 23.3, 31.01,
　　　　73/23.2, 23.21, 23.34, 23.29, 23.28, 24.02;
　　　　422/83; 436/62, 68; 204/401, 408

[56] References Cited

U.S. PATENT DOCUMENTS

| | | | |
|---|---|---|---|
| 3,300,282 | 1/1967 | Risk et al. | 73/23.2 X |
| 3,585,842 | 6/1971 | Roof | 73/23.2 |
| 5,065,613 | 11/1991 | Lehnert et al. | 73/23.2 |
| 5,270,009 | 12/1993 | Nakamori et al. | 73/16 |

*Primary Examiner*—Michael J. Brock
*Attorney, Agent, or Firm*—Richard J. Hicks

[57] ABSTRACT

An apparatus and method for measuring differential oxygen concentration between two flowing gas streams is described. A reference gas and a sample gas in separate gas flow paths are passed, at selected temperature, pressure and flow rate over a respective one of a pair of electrically connected oxygen sensors which produce an output signal proportional to the differential oxygen concentration between the sensors. The output signal may be amplified and recorded by any conventional means. An internal calibration system is also described.

15 Claims, 9 Drawing Sheets

METHOD AND INSTRUMENT FOR MEASURING DIFFERENTIAL OXYGEN CONCENTRATION BETWEEN TWO FLOWING GAS STREAMS

FIELD OF INVENTION

The invention relates to a method and an instrument for measuring the difference in concentration of $O_2$ between two flowing gas streams, and use of the instrument to measure the rate of $O_2$ production or consumption from living or non-living materials. The instrument differs from previous instruments designed for this purpose in that it can resolve $O_2$ differentials of less than 5 ppm $O_2$ in the presence of background $pO_2$ from 100 ppm to 100%, is compact, easily calibrated, relatively inexpensive to manufacture, and may be battery powered for use outside of the laboratory environment. The primary use of the instrument is the measurement of respiratory $O_2$ consumption by plants, animals and micro-organisms, but it may also be used for respiratory studies on humans, studies of $O_2$-producing photosynthetic cells, and for monitoring small $O_2$ concentration differentials relative to a reference gas in biotic or abiotic systems.

BACKGROUND OF INVENTION AND PRIOR ART

Oxygen is essential to the survival of all cells which respire aerobically, and measurement of $O_2$ consumption rate by cells, is frequently used as an index of the cells' metabolic activity. $CO_2$ is produced during respiration, and in most cells under normal aerobic conditions, the ratio of $CO_2$ produced to $O_2$ consumed is close to unity. This ratio is termed the respiratory quotient (RQ) and it is an important indicator of the cells' metabolic state. For example, RQ changes depending on the nature of the respiratory substrate used by the cells, and increases greatly when the cells are subjected to anaerobic stress. Measurements of respiratory $O_2$ consumption, $CO_2$ production and RQ are used in studies ranging from human exercise physiology to bacterial degradation of organic waste materials.

Green plants also respire aerobically, but in the light their photosynthetic activity results in a net production, rather than consumption, of $O_2$. Measurement of $O_2$ production from plants is often used as an assay of photosynthetic activity. During photosynthesis, plants convert atmospheric $CO_2$ to organic carbon, and water is converted to $O_2$ gas. The ratio of $CO_2$ consumed to $O_2$ produced by the plant is termed the photosynthetic quotient (PQ) and, like the RQ, this value is an important indicator of the plant's metabolic condition.

The most common method of monitoring $O_2$ consumption or production from cells is to place an organism, tissue or cell suspension in a chamber (cuvette) containing a known concentration of $O_2$, and to monitor changes in the $O_2$ concentration within the cuvette with time. This can be done by either "closed system" or "open system" gas exchange methods. The closed system method involves sealing the biological sample in the cuvette and then taking samples of the air from the cuvette at measured time intervals. Each air sample is analyzed for $O_2$ concentration, and the change of $O_2$ concentration with time can be used to estimate the mean rate of $O_2$ production or consumption between sampling periods. In its simplest form, the closed system assay involves only an initial and a final measurement of $O_2$ concentration, and the difference in the amount of $O_2$ in the cuvette is divided by the incubation period to give the rate of $O_2$ exchange during the assay period.

The closed system assay for measuring $O_2$ exchange has several limitations, the most important of which is that rates of $O_2$ exchange cannot be measured in real time. Therefore, any changes in the rate of biological $O_2$ exchange cannot be observed as they occur. Also, unless the atmosphere of the cuvette is sampled at regular intervals, any short-term perturbations in the rate cannot be detected. Such perturbations are likely to occur in a sealed cuvette since respiration rate and photosynthesis in many cells are affected by $pO_2$, and $pO_2$ will change in the cuvette as $O_2$ is either depleted or evolved. To overcome these problems, open gas exchange systems have been developed to provide continuous measurements of $O_2$ exchange under either steady or non-steady state conditions.

Measurement of $O_2$ exchange in an open gas exchange system involves placing the biological sample in a cuvette through which gas of known composition flows at a measured rate. The $O_2$ concentration of the effluent gas from the cuvette is monitored by an $O_2$ analyzer, and the difference in $O_2$ concentration between the input and effluent gases multiplied by the flow rate through the cuvette gives a measure of the rate of $O_2$ exchange. If the $O_2$ analyzer used in the open system is itself a flow-through instrument, the $O_2$ concentration in the effluent gas stream can be monitored continuously, and real-time measurements of $O_2$ exchange can be performed.

The most accurate method of measuring $O_2$ exchange in an open flow gas exchange system is to use a differential $O_2$ analyzer. Such instruments continuously monitor the difference in $O_2$ concentration between a reference gas stream and a stream of the same gas composition which has passed through a cuvette containing the material under study. The most sensitive differential $O_2$ analyzers currently available contain either paramagnetic $O_2$ sensors (e.g. the Oxygor 6N, Maihak AG, Hamburg, Germany) or zirconium oxide sensors (e.g. Model S-3A/II, Servomex Company, MA 02062, U.S.A.). However, the sensitivities of these instruments are limited. The Oxygor 6N can resolve a minimum $O_2$ differential of only 100 ppm $O_2$ (which equals 10 Pa at 1 Atm total pressure) when air (approx. 20.9 kPa $O_2$) is used as the reference gas. Under the same conditions, the Servomex S-3A/II has an accuracy limit of only $\pm 3$ pa $O_2$ in differential mode. Therefore, neither instrument has the sensitivity required to measure the very small $O_2$ differentials that may occur when the biological sample under study has a low metabolic rate. Also, both types of differential $O_2$ analyzer are essentially laboratory-based instruments which are not readily adaptable for field use, each requiring AC power and stable environmental conditions for most accurate function. They also require calibration by laboratory-based calibration systems involving compressed gases and/or gas mixing instruments. This adds to the considerable expense of the analyzers.

Since differential $O_2$ analyzers are relatively insensitive, many researchers use closed gas exchange systems to study organisms with low rates of $O_2$ exchange. For example, the Micro-Oxymax Respirometer developed by Columbus Instruments International Corporation (Columbus, Ohio 43204, U.S.A.) is among the most sensitive closed system device currently available for measuring $O_2$ exchange from living organisms. This device is capable of measuring an $O_2$ consumption rate of 0.2 µl $O_2$/h over a 24 hour period. However, at this level of sensitivity, the user can obtain only a single average measurement of $O_2$ exchange over the 24 h period, and is unable to observe respiratory dynamics during the measurement. Use of the Micro-Oxymax Respirometer is further limited in that the gas supplied to the cuvette cannot have a partial pressure of $O_2$ ($pO_2$) exceeding 30 kPa. Therefore, the instrument cannot be used in experiments which require elevation of $PO_2$ beyond this limit (e.g. the measurement of $O_2$-saturated respiration rates in cells with respiratory rates limited by $O_2$ diffusion, or the measurement of photosynthesis at high rates of photorespiration that occur at elevated $pO_2$). Like commercially available differential $O_2$ analyzers, the Micro-Oxymax Respirometer is a laboratory-based instrument that is not readily adaptable for field use. Its purchase price is also in the same range as that of available differential $O_2$ analyzers.

The limitations of available differential and closed system $O_2$ analyzers indicate the need for an $O_2$ analyzer that can provide continuous measurements of very small (less than 1 Pa) $O_2$ differentials between two flowing gas streams. Such an analyzer should be able to measure $O_2$ differentials between reference and sample gas streams containing any $pO_2$ up to 100 kPa, and should be sensitive enough to resolve a $pO_2$ difference of as little as 1 Pa between these gas streams irrespective of the $pO_2$ in the reference gas. The instrument should be inexpensive, easily calibrated, preferably by an internal calibration system, and readily adaptable for field use. Also, the instrument should be readily adaptable for simultaneous measurements of differential $pO_2$ and $CO_2$, enabling the user to obtain a direct measure of the respiratory quotient or photosynthetic quotient of the experimental material.

OBJECT OF THE INVENTION

It is an object of the present invention to provide an inexpensive differential $O_2$ analyzer, adaptable for use in the laboratory or the field, that is capable of continuously measuring $O_2$ differentials between flowing reference and sample gas streams containing any $pO_2$, and capable of resolving such differentials of less than 1 Pa in a background $pO_2$ from 10 Pa to 100 kPa $O_2$.

It is a further object of the present invention to provide a differential $O_2$ analyzer which incorporates environmental sensors to monitor the conditions under which the analyzer is used, so that the data from these sensors may be used to automatically correct the output of the analyzer as environmental conditions vary.

It is a further object of the present invention to provide a method by which the said differential $O_2$ analyzer may be calibrated by an integral calibration system that does not require the use of ancillary gas-mixing apparatus.

It is a further object of the present invention to provide a differential $O_2$ analyzer incorporating, within a single instrument, a system to measure both the differential $pO_2$ and the differential $pCO_2$ between reference and sample gas streams.

BRIEF STATEMENT OF INVENTION

By one aspect of this invention there is provided an apparatus for measuring differential oxygen concentrations between two flowing gas streams, comprising; temperature-controlled housing means having first and second gas flow paths therethrough, each said flow path having means to introduce a selected gas stream, means to control pressure and flow rate of said gas stream; means to generate signals representative of pressure and oxygen concentration differentials between said gas streams; and computer means to monitor said pressure, flow and temperature and said signals representative of said differential pressure and oxygen concentration so as to measure and record differential oxygen concentration between said gas streams.

By another aspect of this invention there is provided a method for measuring differential oxygen concentration between two flowing gas streams, at least one of which contains oxygen, comprising; passing each said gas stream at a selected temperature, pressure and flow rate over a respective one of a pair of electrically interconnected oxygen sensors, so as to produce an output signal that is proportional to the differential oxygen concentration between said sensors.

DETAILED DESCRIPTION OF PREFERRED EMBODIMENTS

A Typical Open Circuit Gas Exchange System.

Figure 1:
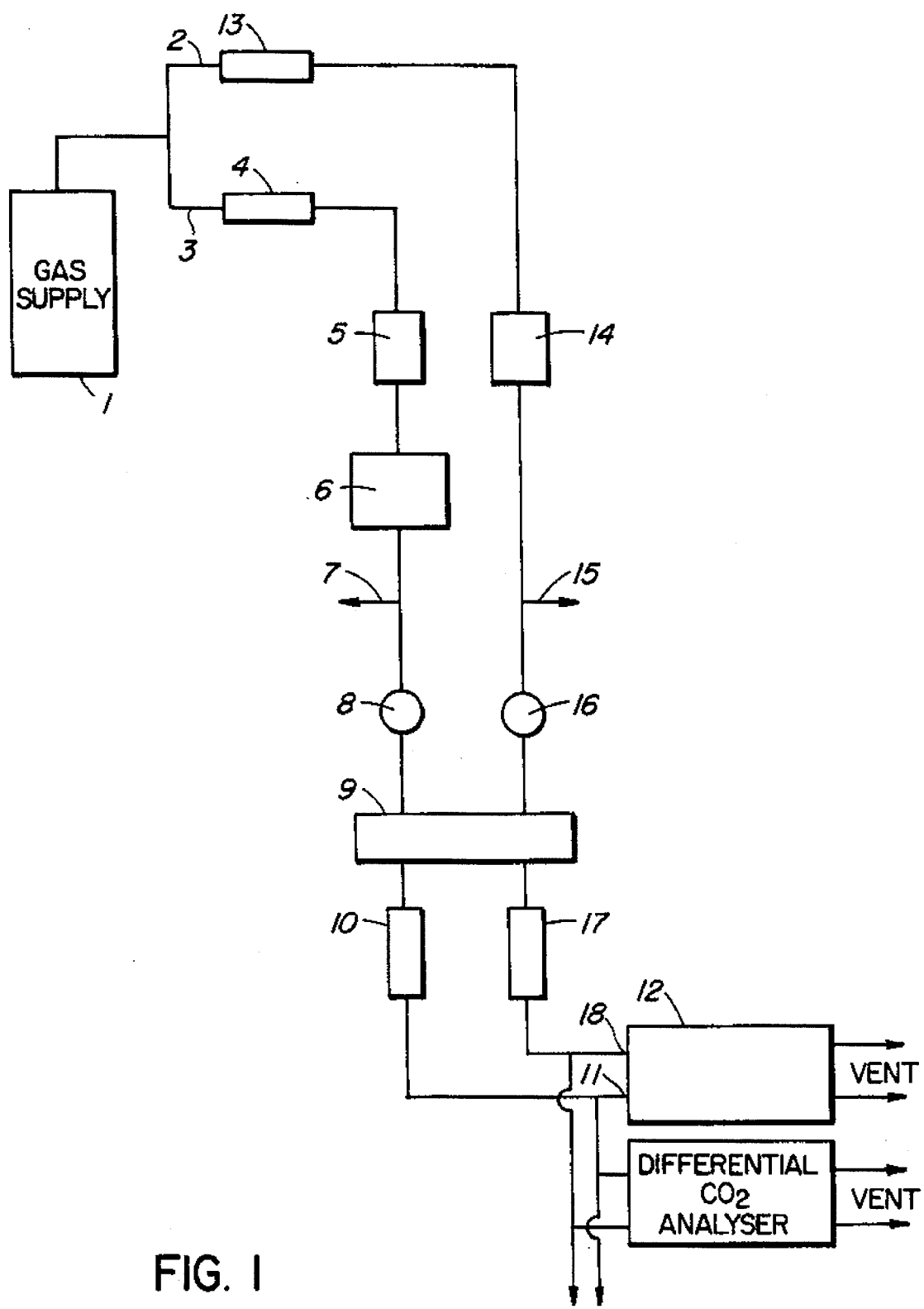
FIG. 1 is a diagram of a typical open-flow gas exchange system incorporating the differential $O_2$ analyzer and showing how a differential $CO_2$ analyzer may be incorporated into the system to measure RQ or PQ.

The differential $O_2$ analyzer is designed for use in an open flow gas exchange system of the type shown in FIG. 1. A supply of gas 1 (air or a mixed gas) containing $O_2$ is divided into a reference stream 2 and a sample stream 3. The flow rate of the sample stream is measured using a flow meter 4, and the gas passes through a humidification system 5 before entering a cuvette 6 containing material which either produces or consumes $O_2$. After passage through the cuvette, a proportion of the gas is vented to atmosphere 7, and the remainder is dried by being drawn, by a pump 8, through a condenser in an ice water bath 9 and through a column of magnesium perchlorate 10. The gas then enters the sample side 11 of the $O_2$ analyzer 12.

The flow rate of the reference gas stream is measured by a flow meter 13 and the gas then enters a humidifier 14 of the same type as that in the sample gas stream. A proportion of the reference gas is vented to atmosphere 15, and the remainder is dried by being drawn, by a pump 16, through a condenser in an ice water bath 9 and through a magnesium perchlorate column 17. The reference gas then enters the reference side 18 of the $O_2$ analyzer. After passage through the analyzer both the reference and sample gas streams are vented to atmosphere.

In an alternative embodiment, the differential $O_2$ analyzer could be used to measure the $O_2$ concentration of a gas collected in a specific environment, rather than the $O_2$ concentration of a gas modified by passage through a cuvette containing living material. Such measurements would be important to atmospheric monitoring in which information is required on diurnal, seasonal or regional fluctuations in atmospheric $pO_2$. In this application the reference gas used in the analyzer would be a bottled, or mixed, gas of known $pO_2$, and the sample gas would be pumped from a container directly to the dehumidifier of the gas exchange system before entering the sample side of the differential analyzer.

Design of the Differential $O_2$ Analyzer.

Figure 2:
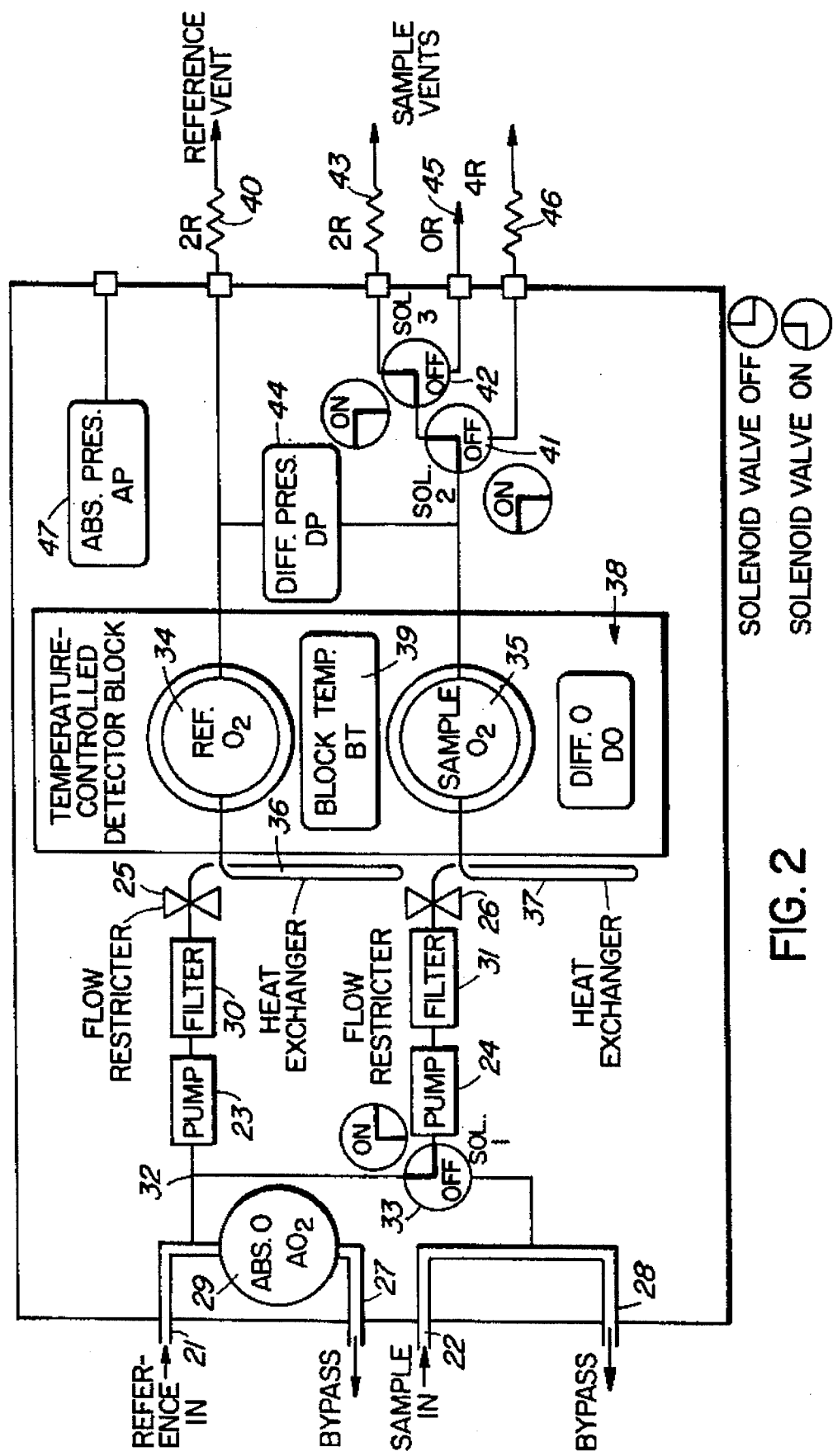
FIG. 2 shows an arrangement of components within the differential $O_2$ analyzer and the flow of gases through the instrument.

A block diagram of the differential $O_2$ analyzer is shown in FIG. 2. A proportion of the reference 21 and sample 22 gas streams, which have been dried to a similar extent by passage through the ice water bath and magnesium perchlorate columns, are drawn into the analyzer by pumps 23 and 24, respectively, which work against downstream flow restrictors 25 and 26. The remainder of the gases vent to atmosphere through by-passes 27 and 28. An $O_2$ sensor 29 (Model KE-25, Figaro U.S.A. Inc., Illinois, U.S.A.) in the reference gas by-pass line measures the absolute $O_2$ concentration in the reference stream. Particulate matter is removed from both gas streams by glass wool filters 30 and 31 positioned adjacent to the flow restrictors. The reference stream is divided at a tee-piece 32, one branch entering Pump 23, and the other entering solenoid 33. When solenoid 33 is in the "on" position, the analyzer is in measurement mode and all of the reference gas passes through pump 23, and through the reference side of the differential analyzer. In this configuration, the sample gas entering solenoid 33 is pumped through the sample side of the analyzer. When solenoid 33 is in the "off" position, reference gas is pumped through both the reference and sample sides of the analyzer, and the instrument is in zero mode. In either mode, the gases which pass through the reference 34 and sample 35 $O_2$ sensors (Model KE-25 Figaro U.S.A., Illinois, U.S.A.) first enter heat exchangers 36 and 37, integrated into the temperature-controlled detector block 38 in which the sensors are housed. For optimal operation, the temperature of the block should be maintained above the highest ambient temperature to which the instrument is likely to be exposed, but its normal operating temperature is 40° C. This temperature is monitored by a thermistor 39, or other temperature sensitive device, integrated into the sensor block.

The reference gas stream exits through a detachable flow restrictor 40 in the form of a stainless steel tube with a small orifice. When both solenoid 41 and 42 are in the "off" position, the sample stream exits through a detachable flow restrictor 43 having physical properties similar to those of flow restrictor 40 located in the reference gas flow stream. Therefore, at the same gas flow rate in the reference and sample flow streams, the flow restrictors will provide similar backpressures on the differential $O_2$ sensors and the differential pressure sensor 44 will read near zero. When solenoid 42 is activated, and solenoid 41 is off, the sample gas stream is vented directly to atmosphere at 45, resulting in a lower backpressure in the sample gas stream relative to that in the reference gas stream, the magnitude of which is measured by the differential pressure sensor 44. By selecting flow restrictors having different characteristics, or by controlling the gas flow rate of the reference and sample streams, the user can regulate the magnitude of the pressure differential obtained when solenoid 41 is activated.

When solenoid 41 is activated and solenoid 42 is off, the sample gas stream is vented through a flow restrictor 46 having a resistance to gas flow approximately twice that of flow restrictors 40 and 43. This results in an increase in the differential pressure in the sample gas stream relative to the reference gas stream, the magnitude of which is measured by the differential pressure sensor 44.

The increases or decreases in differential pressure in the sample gas stream created by the activation of solenoid 41 or solenoid 42 results in small changes in the $O_2$ concentration in the sample side of the analyzer which can be detected by the differential $O_2$ sensor. This is the basis for the integrated calibration system of the analyser. To ensure that the changes in the backpressure on the sample gas stream has a minimal effect on the flow rate of the gas stream, it is recommended that the resistances of the flow restrictors 40, 43 and 46 are less than 15% of the resistance of the flow restrictors 25 and 26 which are located immediately downstream of pumps 23 and 24 and filters 30 and 31.

During operation of the $O_2$ analyzer, atmospheric pressure is monitored by an absolute pressure sensor 47 which has its own port to the exterior of the instrument. Measurement of atmospheric pressure is essential for the calculation of $O_2$ concentration in the reference gas stream.

In an alternative embodiment of the instrument (FIG. 3) the design of the temperature-controlled sensor block 38 is identical to that shown in FIG. 2, but the flow path of the reference gas 21 and sample gas 22, through the instrument is different. In the alternative embodiment both the reference gas and sample gas are drawn into the instrument by a single pump 48 located just before the point 49 at which the gases vent from the instrument. A void volume 50 of approximately 10 $cm^3$ is incorporated into the gas line just before the pump to dampen any oscillations in flow rate.

The flow of gases through the instrument is controlled by solenoid valves 51, 52 and 53 and the activation and deactivation of these differ depending on the use of the instrument in calibration mode or measurement mode. To calibrate the instrument zero conditions are first established by flushing reference gas through both the reference and sample side of the instrument. The normally closed solenoid 51 is deactivated so that the sample gas 22 is blocked from entering the sample side of the analyzer and vents to atmosphere through by-pass 28. A sample of the reference gas 21 enters a tee-piece 32 and is drawn through both the reference and sample sides of the instrument by pump 48. The remainder of the reference gas passes through an absolute $O_2$ sensor 29 and vents from the instrument at by-pass 27. In the sample side of the instrument, the reference gas enters a tee-piece 54 connected to solenoid valve 52. This valve is closed when deactivated and diverts the reference gas through a flow restrictor 55 of the same type as those described for the embodiment of the instrument shown in FIG. 2. Having passed through the flow restrictor 55, the gas enters a tee-piece 56 attached to a solenoid valve 53 which is open when deactivated. When open, this valve allows the gas to pass without further resistance to the sample $O_2$ gas sensor 35 in the temperature-controlled detector block 38. After passing through $O_2$ sensor 35, the reference gas exits the detector block and is drawn by the pump through a flow restrictor 57 having a resistance approximately 20 times that of flow restrictor 55. After exiting flow restrictor 57, the reference gas in the sample side of the instrument is combined at tee-piece 59 with gas that has passed through the reference side of the instrument, and the mixed gas is pumped from the instrument via the void volume 50. With solenoid valves 51, 52 and 53 in the configuration described above, a proportion of the reference gas entering tee-piece 32 passes into the reference side of the instrument via a needle valve 61. The gas then enters the reference $O_2$ sensor 34 in the detector block 38 and is drawn from the detector block through a flow restrictor 60 having a similar resistance to the flow restrictor 57 in the corresponding position in the sample side of the instrument. The reference gas is then combined at tee-piece 59 with the reference gas that has passed through the sample side of the instrument, and the combined gases are pumped from the instrument at vent 49. The flow rate of gas through the instrument is controlled by pump 48, and this is calibrated by means of a different pressure sensor 58 located between the input and output ports of flow restrictor 59. At high flow rate, the pressure differential across flow restrictor 59 is greater than at lower flow rates, and the relationship between pressure differential and flow rate is stored in the instrument software so that the voltage output of differential pressure sensor 58 can be used to monitor and control the speed of the pump.

With reference gas flowing in both the reference and sample sides of the instrument, the differential $O_2$ concentration between $O_2$ sensors 34 and 35 will be zero only if there is no differential pressure between the gases in each sensor. The differential pressure sensor 44 positioned between the reference and sample gas streams monitors the pressure differential between the reference and sample sides of the instrument, and the needle valve 61 in the reference line can be adjusted to set this pressure differential to zero.

When zero conditions have been established, the differential $O_2$ analyser may be calibrated by varying the pressure of the reference gas in the sample side of the instrument. To increase the pressure of gas in the sample $O_2$ sensor relative to that in the reference sensor, and thereby increase $PO_2$ in the sample sensor, solenoid 52 is activated. When activated solenoid 52 is in the open position, and allows the reference gas to flow without restriction to the sample $O_2$ sensor. Under these conditions the differential pressure sensor 44 reads a pressure differential which is related to the $O_2$ concentration differential between the sample and reference $O_2$ sensors.

To reduce the pressure in the sample gas line relative to that in the reference gas line, and thereby reduce the $O_2$ concentration in sample sensor 35, solenoid 52 is deactivated (closed) and solenoid 53 is activated (also closed). With solenoid 52 and 53 both in the closed position, the reference gas must flow through flow restrictor 55, and an additional flow restrictor 62 with the same resistance before entering sample $O_2$ sensor 35. By doubling the resistance in the sample side of the instrument the gas pressure in the sample $O_2$ sensor is decreased. The differential pressure sensor 44 monitors the resulting pressure differential and the differential $O_2$ analyser produces a signal proportional to the differential $O_2$ concentration between the two sensors. The calibration procedure therefore involves establishing a zero condition, then performing a two point calibration involving both higher and lower $pO_2$ conditions in the sample $O_2$ sensor relative to the reference $O_2$ sensor. Measurement of the differential pressure between the sensors allows calculation of the differential $pO_2$ values that these pressure changes cause.

In measurement mode, solenoid 51 is activated (opened) to allow sample gas to flow through the sample side of the instrument. Solenoid 52 is closed and solenoid 53 is open so that the sample gas passes only through flow restrictor 55. Under these conditions there will be no differential pressure between the reference and sample gas streams, since the resistance of flow restrictor 55 was balanced by adjustment of needle valve 61 in the reference gas stream during the calibration procedure. Therefore, any signal generated from the differential $O_2$ analyser will be due only to the differential $pO_2$ between the reference and sample $O_2$ sensors, and not influenced by pressure effects.

In either embodiment of the instrument, the differential $O_2$ analyzer may be calibrated and operated using computer control. The outputs of the absolute $0_2$ sensor, the reference and sample $O_2$ sensors, the block temperature thermistor, the absolute pressure sensor and the differential pressure sensor undergo analog to digital conversion and the digital values are stored for use in subsequent calculations. The speed of pumps 23 and 24, (FIG. 2) or pump 48 in the alternative embodiment (FIG. 3) and the block temperature are controlled by an analog output from a digital to analogue converter, or by digital control of a voltage divider supplying power to the pumps. In addition, the positions of solenoids 33, 41, and 42 (FIG. 2) or solenoids 51, 52 and 53 in the alternative embodiment of the instrument (FIG. 3) are digitally controlled. The calibration procedure for the embodiment of the differential $0_2$ analyser shown in FIG. 2 is described in detail below, as are the mathematical analyses required for calibration and use of both embodiments of the instrument.

Design of the Sensor Block

Figure 3:
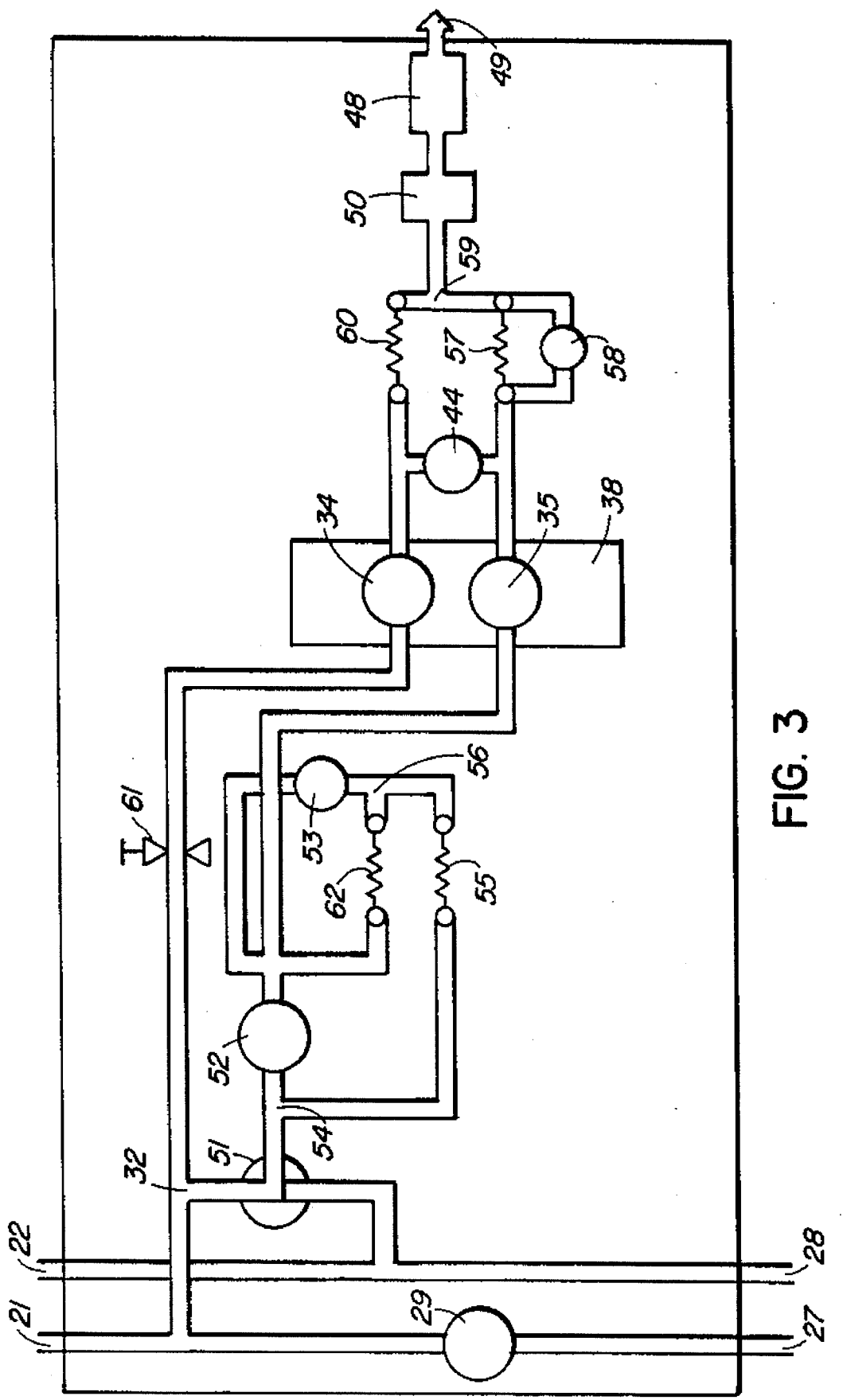
FIG. 3 is an alternative arrangement of components, similar to FIG. 2.
Figure 4:
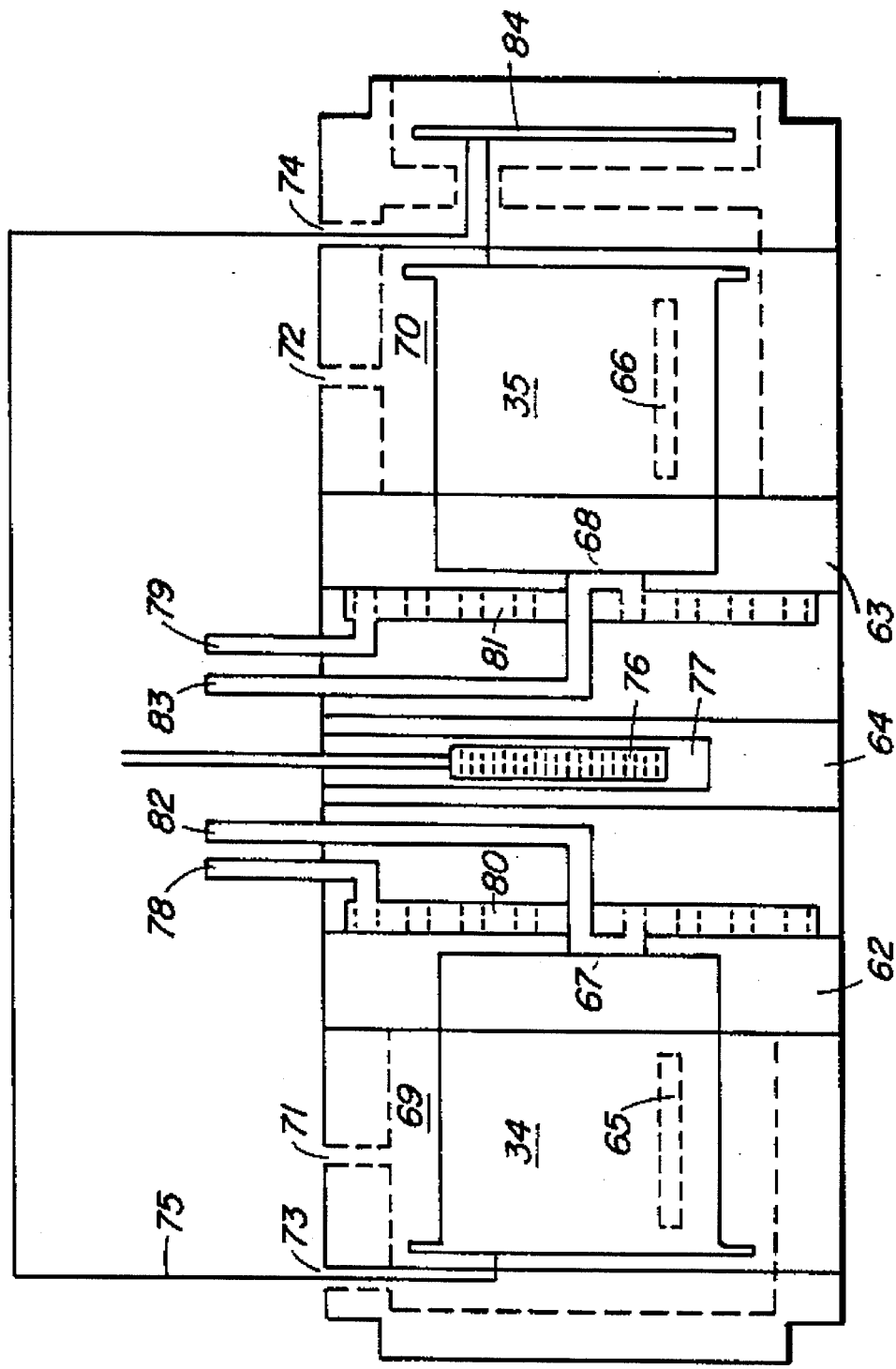
FIG. 4 shows details of the sensor block that encloses the $O_2$ sensors to be used in the differential mode.

The design of the temperature-controlled sensor block (38; FIG. 2 and FIG. 3) is shown in FIG. 4. The reference 34 and sample 35 $O_2$ sensors are located in identical housings 62 and 63, respectively, constructed of a heat-conducting material, such as aluminum or stainless steel. The two housings are joined at a centre plate 64. The reference and sample sensors are oriented in their housings so that their lead anodes 65 and 66 are located towards the base of the instrument. The sensing heads 67 and 68 of the $O_2$ sensors are held tightly in position by the body of their respective housings, while the remaining part of the sensors fit into air-filled cavities 69 and 70 within the housings. The air in these cavities is continous with the ambient atmosphere within the instrument via ports 71 and 72. Other ports 73 and 74 through the sensor housings into the air-filled cavities 69 and 70 allow passage of the electrical connections 75 between the sensors. The entire sensor block, consisting of the two joined housings, is wrapped in heating foil (not shown), the temperature of which is controlled by a power supply. A resistive temperature device 76, submerged in a heat transfer gel in a cavity 77 within the centre plate of the sensor block, continuously monitors block temperature during use.

Reference and sample gas enter the sensor block by ports 78 and 79, respectively. The gases then pass through heat exchangers 80 and 81 consisting of circular gas channels within the sensor housings which direct the gases by a tortuous route to the sensing heads 67 and 68 of their respective $O_2$ analysers 34 and 35. The gases reach the temperature of the sensor block during passage through the heat exchangers, and after passing across the $O_2$ sensors they leave the sensor block by a direct route through ports 82 and 83.

The pre-amplifer 84 (and see FIG. 5) which conditions the signal from the differential $O_2$ analyser is temperature sensitive and is therefore maintained at a constant temperature by incorporation within the sensor block.

The Differential $O_2$ Analyzer: Design and Principle of Operation.

(a) Electrical Configuration of the Differential $O_2$ Sensor.

The reference and sample $O_2$ sensors (preferred embodiment is Model KE-25, Figaro U.S.A. Inc., Illinois, U.S.A.) used within the differential $O_2$ analyzer-operate on the principle of a lead-oxygen battery. Each contains a lead anode, an oxygen cathode (which is made of gold) and a weak acid electrolyte. $O_2$ passing across the surface of the sensor diffuses through a Teflon FEP membrane and is reduced electrochemically at the gold electrode. As supplied from the manufacturer, each sensor contained a resistor and a thermistor connected in series (with a total resistance of about 1.2 kOhms) between the anode and the cathode so that the voltage differential is proportional to the $O_2$ concentration at the teflon membrane despite variations in temperature.

Figure 5:
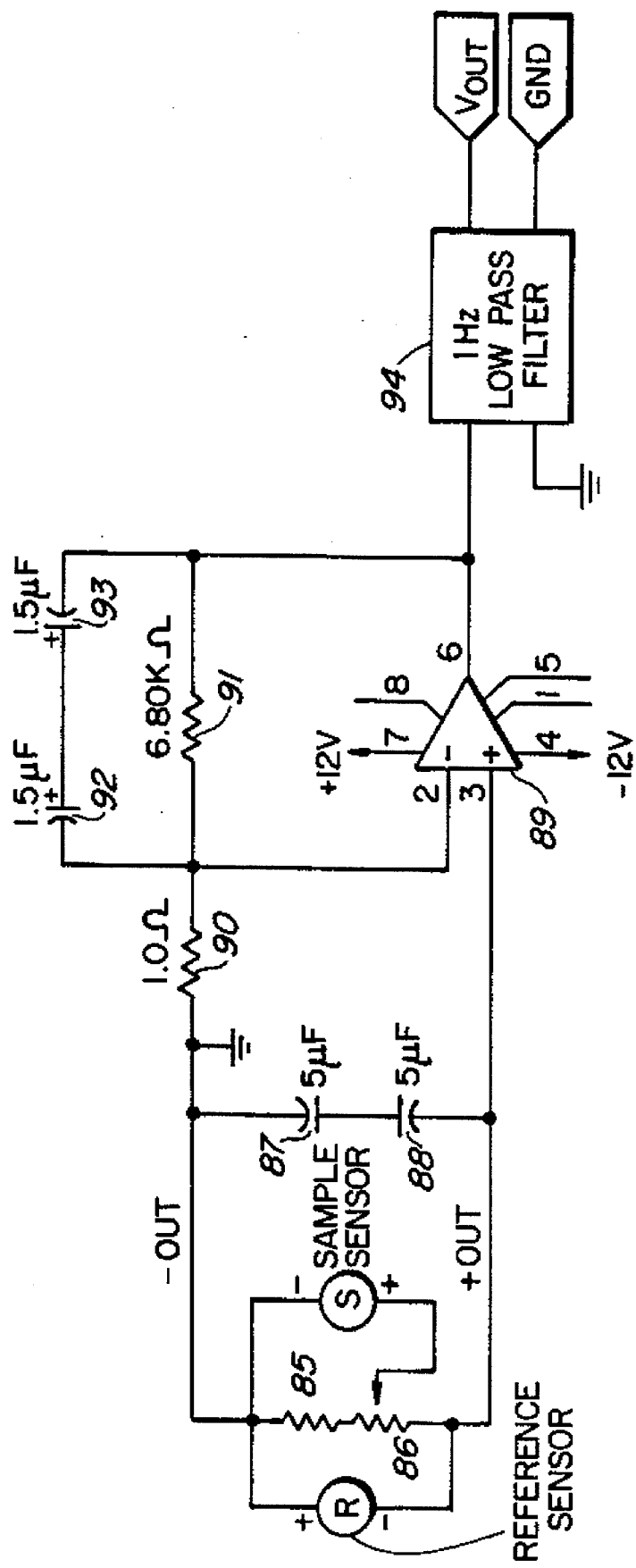
FIG. 5 shows the electrical schematics for connecting reference and sample $O_2$ sensors to provide a differential output voltage which can be balanced if the sensors differ in their output at a given $pO_2$, and the electrical circuit for amplifying the output signal from the $O_2$ sensors.

For use in the differential $O_2$ analyser, two individual sensors were modified and placed in an electrical circuit, as shown in FIG. 5, such that the output of the circuit was proportional to the differential $O_2$ concentration between the two sensors. The modification and features of the differential sensors include:

(i) The connection between the internal resistors of each sensor was severed and the leads connected in parallel across a fixed 800 ohm resistor 85, and a 200 ohm potentiometer 86, as shown in FIG. 5.

(ii) The sensor with the larger current output at a given $pO_2$ was placed in the circuit such that the anode was connected to the wiper on the 200 ohm potentiometer. Typically, the current produced by the reference sensor was approximately 15 µA at 40° C. and 20 kPa $O_2$, while that of the sample sensor was 20 µA under the same conditions.

(iii) When gas streams having the same $pO_2$ and atmospheric pressure were presented to both sensors, the potentiometer 86 was adjusted so that the differential output of the circuit was zero volts.

(iv) Increases or decreases in the $pO_2$ at the sample sensor altered the current flow through the fixed resistor 85 and potentiometer 86, which in turn altered the output voltage differential.

(b) Amplification of differential voltage.

The voltage output of the differential $O_2$ sensor is inherently linear with the differential $pO_2$ between the reference and sample gas streams, but the voltages produced are very small. For example, a $pO_2$ differential of 10 Pa (equivalent to ca. 100 ppm $O_2$ at 1 atmosphere pressure) between the reference and analysis sensors produces a voltage differential of only 12.5 µV. A low noise µV amplifier, such as that shown in FIG. 5 is required to boost the signal into a measurable range.

First, the positive and negative outputs from the sensor circuit are DC filtered by passage through two tantalum 5 µF capacitors 87 and 88 arranged back to back in series. The negative output is connected to ground, and the positive output enters a TLC1150 operational amplifier 89 configured as a non-inverting amplifier. This has a voltage gain factor of 6800 which is achieved with temperature stable precision resistors. The input resistor 90 has a resistance of 1 Ohm, and the feedback resistor 91 has a resistance of 6.8 kOhm. Two 1.5 µF tantalum capacitors 92 and 93 arranged back to back in series with each other, and in parallel with the 6.8 kOhm resistor prevent amplification of high frequency noise. The outputs from the TLC1150 operational amplifier enter a 1 Hz low pass filter 94 to further reduce noise. The outputs from the low pass filter can be connected to an analogue recording device, such as a chart recorder, or to an analogue to digital converter for data logging by a computer (not shown).

Calibration of the Differential Oxygen Analyzer

Calibration of any differential $O_2$ analyzer requires that a reference gas with a known $pO_2$ be passed through the reference $O_2$ sensor while gases containing known $pO_2$s, different from that in the reference gas, are passed through the sample sensor. To check linearity of the analyzer response, at least a three point calibration should be carried out. This should include $pO_2$ values above and below that in the reference gas if positive and negative $O_2$ differentials are to be measured during use of the analyzer. Also, the calibration should be performed to encompass the range of $pO_2$ differentials that the instrument is required to measure. Standard gases used in calibrations may be mixed in the laboratory using high precision gas mixing pumps such as Wosthoff pumps, or by mixing gases using electronic mass flow controllers. Both of these options are very expensive. Alternatively, standard gases may be purchased from a gas supply company, but this too is very expensive in the long term. It should also be noted that these current methods of calibration require the use of laboratory-based ancillary equipment. In contrast, the embodiments of the differential $O_2$ analyzer shown in FIG. 2 and FIG. 3 have an integrated calibration routine that does not involve gas mixing, and which does not require the use of additional laboratory facilities. Dry air is used as the calibration gas, and the same air is passed through the reference and sample $O_2$ sensors by deactivation of solenoid 33 (FIG. 2) or solenoid 51 (FIG. 3), but the $pO_2$ of the air in the sample gas stream is varied by applying different gas pressures on the sample $O_2$ sensor. To calculate differentials of $pO_2$ resulting from pressure differentials between the reference and sample sensors requires measurement of the environmental conditions in which the instrument is used. Calibration of the environmental sensors within the analyzer, and use of the data they provide to calculate $O_2$ differentials is described below.

(a) Measurement of atmospheric pressure.

For accurate calibration of the differential $O_2$ analyzer, the absolute partial pressure of $O_2$ in the air entering the instrument must be known in units of kPa. This $pO_2$ will vary depending on the ambient atmospheric pressure, since air at higher pressure contains a greater number of molecules of $O_2$ per unit volume than air at lower pressure (e.g. air containing 20% $O_2$ has a $pO_2$ of 24 kPa at an atmospheric pressure of 120 kPa, but a $pO_2$ of 20 kPa at 100 kPa atmospheric pressure). The analyzer therefore incorporates an absolute pressure sensor (47; FIG. 2) to measure ambient atmospheric pressure. The voltage output of this absolute pressure sensor itself must be converted to units of kPa pressure, which requires calibration of the sensor using a Hg manometer. This is done during assembly of the analyzer, but the calibration may be modified by the user through software.

A two point calibration procedure for the absolute pressure sensor is used in which the voltage output is measured under ambient pressure conditions, and when zero pressure is established by attaching the sensor to a vacuum pump. Ambient pressure is measured in units of mm Hg by a mercury manometer, and this value is converted to units of kPa taking into account the effects of ambient temperature on the relative expansion of Hg and glass within the barometer, and latitude-dependent gravitational force on the mm Hg reading. Ambient temperature is read from the instrument thermistor within the analyzer (39: FIG. 2). The temperature correction factor is stored as a linear regression in software, and the gravitational correction factor as a third order polynomial. These correction factors allow for an accurate conversion of mm Hg to kPa irrespective of the temperature or geographical location in which the instrument is used. The relationship between kPa and voltage output of the absolute pressure sensor is stored as a linear regression in software. The absolute pressure of the air within the reference sensor is the sum of the ambient pressure plus the back pressure exerted on the sensor by the flow restrictor on the reference gas outlet port (40; FIG. 2). This backpressure is measured during calibration of reference gas flow rate as described in (d) below.

(b) Calibration of the absolute $O_2$ sensor.

The absolute $O_2$ sensor in the reference gas stream (35; FIG. 2) is calibrated during assembly of the analyzer, but the calibration may be altered in software by the user. A two point calibration is made in which the voltage output of the sensor is measured at 100% $O_2$ and 0% $O_2$ (pure N2). Percentage $O_2$ at the pressure maintained within the reference $O_2$ sensor is converted to kPa $O_2$ as described in (a) above. A linear regression of absolute $O_2$ sensor voltage output against kPa $O_2$ is stored in software and used to convert voltage output to kPa $O_2$ at any input $pO_2$ and pressure.

(c) Calibration of differential pressure sensor.

The differential pressure sensor is calibrated by a three point calibration in which zero, positive and negative pressure differentials are applied between the reference and analysis $O_2$ sensors. The absolute pressure differentials are measured by a water manometer placed between the reference and sample gas streams, and the pressure units are converted from mm $H_2O$ to Pa taking into account the gravitational correction factor due to latitude as described in (b) above for conversion of mm Hg to kPa. A temperature correction factor is not included in this conversion of units since it is assumed that glass and water have similar temperature dependent coefficients of expansion. A linear regression is run of differential pressure (Pa) against the voltage output of the differential pressure sensor, which allows differential pressures to be estimated within the range of pressures used in the calibration routine.

In the embodiment of the differential $O_2$ analyser shown in FIG. 2, differential pressures between the sample and reference $O_2$ sensors are achieved by diverting the sample gas stream through different flow restrictors before it vents from the instrument. The reference gas stream always vents through a fixed resistance (40; FIG. 2) and, under normal operating conditions for the analyzer, solenoids 41 and 42 (FIG. 2) are set in the off position so that the sample gas vents through a similar resistance to that in the reference line. This produces a zero pressure differential between the reference and analysis $O_2$ sensors, and the voltage output of the differential pressure sensor reflects this zero. To obtain a positive pressure differential between the sample and reference sensors, solenoid 33 (FIG. 2) is activated so that the sample gas flows through restrictor 26 with a greater back pressure than that in the reference line. To obtain a negative pressure differential between the sample and reference sensors, solenoid 41 (FIG. 2) is deactivated and solenoid 42 (FIG. 2) is activated so that the sample gas vents directly to atmosphere.

The range of backpressures over which the differential pressure sensor is calibrated may be varied by changing the flow restrictors through which the reference and sample gas vent. Since these restrictors consist of detachable tubes with different bore sizes, they are easily replaced by tubes having either narrower or wider bores. Alternatively, tubes of the same bore size, but differing in length, can be used to vary back pressure.

The way in which differential pressures are achieved between the reference and sample $O_2$ sensors in the alternative embodiment of the instrument shown in FIG. 3 has already been described above. The range of pressures over which this embodiment of the analyser may be calibrated can be changed by changing the internal flow restrictors 55 and 56 for restrictors of greater or less resistance.

(d) Calibration of pump speed.

In the embodiment of the differential $O_2$ analyser shown in FIG. 2, the back pressure exerted on the reference and sample $O_2$ sensors is a function of the rate at which the reference (23; FIG. 2) and analysis (24; FIG. 2) pumps sample their respective gases, as well as the magnitude of the flow restrictors through which the gas streams vent to atmosphere. Therefore, it is necessary to set the pump speeds to achieve a zero pressure differential between the sensors when the two gas streams vent through restrictors of similar resistance. To achieve this at a given flow rate it is only necessary to calibrate the reference gas pump while the sample gas pump is inactive. Under these conditions, atmospheric pressure will be maintained in the sample gas line while a positive pressure will occur in the reference gas line. The magnitude of the pressure differential between the two gas lines will be determined by the speed of the reference pump and by the back pressure exerted by the resistor (40; FIG. 2) on the reference gas vent. By varying the pump speed and attaching a zero resistance flow measuring device to the reference gas vent, the relationship between flow rate of the reference gas and the pressure differential between the reference and sample gas lines can be determined. A look-up table can be established in the analyzer software which relates flow rates and pressure differentials for different resistors in the reference stream.

To attain a desired flow rate through the instrument, zero voltage is supplied to the sample pump while voltage supply to the reference pump is increased until the pressure differential corresponding to the desired flow rate of the reference gas is attained. Voltage supply to the sample pump is then increased until a zero pressure differential is obtained between the reference and sample gas streams.

This calibration procedure also allows the total pressure of gas in the reference and analysis sensors to be measured. At a given flow rate with a given resistance in the reference line, the look-up table in the analyzer software will show the amount by which the pressure in the $O_2$ sensors exceeds atmospheric pressure. This excess pressure can then be added to the atmospheric pressure, measured as in (a) above, and be used to calibrate the differential $O_2$ analyzer.

Calibration and control of pump speed in the alternative embodiment of the differential $O_2$ analyser shown in FIG. 3 has already been described above.

(e) Calculation of differential $pO_2$ from differential pressure between the reference and analysis $O_2$ sensors.

Steps (a) to (d) in the calibration routine allow measurement of the total pressure (TP; kPA) of gas in the $O_2$ sensors, the absolute $pO_2$ (AO; kPa) of the gas in the reference sensor and the pressure differential (DP; Pa) between the reference and sample sensors. Differential $pO_2$ (DO; Pa) between the two sensors at a given pressure differential can then be calculated as:

$DO = AO \cdot (DP/TP)$

Measurement of DO and the voltage output from the differential analyzer when positive, negative and zero pressure differentials are applied between the reference and analysis sensors, allows a three point calibration of the analyzer to be performed. This calibration is characterised by a linear regression that is stored in the analyzer software. However, this regression is only valid at the sensor temperature at which the calibration took place since the outputs of the sensors are temperature sensitive. The relationship between sensor output and temperature is described by a third order polynomial which is stored in the analyzer software. This allows values of DO derived from the linear regression to be corrected for changes in temperature of the sensor block. This temperature is set by the user and monitored continuously by a thermistor (39; FIG. 2) embedded within the block during calibration and use of the analyzer. To obtain the most stable output from the analyzer, the block temperature must be set at above ambient temperature. A block temperature of 40° C. is recommended for use of the analyzer in the laboratory, but a somewhat higher block temperature may be necessary if the instrument is exposed to a high heat load in the field.

Calibration checks during analyzer use.

The calibration of the differential $O_2$ analyzer can be checked at any time simply by changing the configuration of solenoids 41 and 42 (FIG. 2), or solenoids 52 and 53 in the alternative embodiment of the instrument (FIG. 3), to create a known pressure differential between the reference and analysis $O_2$ sensors corresponding to a known $O_2$ differential. This procedure can be implemented even when the instrument is being used to measure $O_2$ differentials in measurement mode. Therefore, during an experiment, the user can increase or reduce the $O_2$ differential between the $O_2$ sensors and check whether or not the change in the analyzer output matches that predicted by the current calibration. This comparison could be made by the system software and the user could be warned of significant deviations from the set calibration.

Use of the Differential Oxygen Analyzer

The differential $O_2$ analyzer is compact and can be operated either by DC or AC power. Its calibration requires only a supply of air and can be performed without expense at any time. The air should be completely dried by passage through magnesium perchlorate or other drying agent before it enters the instrument. The analyzer continuously monitors the temperature and pressure of the environment in which it is being used, and the calibration corrects for any fluctuations in these conditions. Therefore, the analyzer is ideally suited for use in the laboratory or the field, unlike other differential $O_2$ analyzers that require stable environmental conditions within a laboratory environment.

Trials of the analyzer have shown that the integral calibration method produces results which are very similar to those obtained from calibrations using Wosthoff precision gas mixing pumps to produce different partial pressures of $O_2$ in $N_2$. The resolution and stability of the instrument is such that a differential $pO_2$ of 0.2 Pa can be measured with 20 kPa $O_2$ flowing through the reference $O_2$ sensor. This represents a 15 to 50 fold greater sensitivity than prior art differential $O_2$ analyzers. Also, the output of the analyzer is constant for a given $O_2$ differential irrespective of the absolute $pO_2$ of the reference gas stream.

Effect of Respiratory Quotient and Photosynthetic Quotient on Oxygen Consumption and Depletion Rates Measured by Differential Oxygen Analysis.

The accuracy with which the differential $O_2$ analyzer can measure rates of $O_2$ exchange from an organism depends on whether or not $O_2$ consumption or production is coupled with the consumption or production of any other gas. Typically, during aerobic respiration under atmospheric conditions, the rate of respiratory $O_2$ uptake by cells is equal to the rate of respiratory $CO_2$ production. In this case, the respiratory quotient (RQ=unit $CO_2$ produced per unit $O_2$ consumed) is unity. However, RQ may be less than unity under aerobic conditions, and can be significantly greater than unity as $CO_2$ evolution increases relative to $O_2$ consumption under anaerobic conditions. RQ is also dependent on the nature of the substrate consumed in respiration. In most higher photosynthetic cells, $CO_2$ fixation is associated with $O_2$ consumption and the photosynthetic quotient (PQ=unit $CO_2$ consumed per unit $O_2$ produced) may be greater or lesser than unity depending on environmental conditions.

The differential $O_2$ content measured between the reference and sample gas streams represents actual rates of $O_2$ evolution or consumption by organisms, cells or tissues only if these rates are balanced exactly by equal rates of consumption and evolution, respectively, of another gas. That is, the total pressure of gases exiting the cuvette must equal the total pressure of gases in the reference gas stream. The errors which occur when $O_2$ exchange is not balanced exactly by the exchange of another gas are best shown by examples.

EXAMPLE 1

Measurement of $O_2$ depletion by an organism having a respiratory quotient of 2.0.

Assume that gas at an atmospheric pressure of 100 kPa, containing 20 kPa $O_2$ in a balance of N2 is supplied to a cuvette at 500 mL/min containing an organism which depletes the supplied $pO_2$ by 10 Pa. At an RQ of 2.0, the organism would add 2 Pa of $CO_2$ to the supplied gas for every 1 Pa of $O_2$ consumed. Therefore, the gas exiting the cuvette 6 (FIG. 1) would have a total pressure of 100 010 Pa, containing 19 990 Pa $0_2$, 20 Pa $CO_2$ and 80 000 Pa N2. The majority of the gas exiting the cuvette is vented to atmosphere via vent 7, and since the total pressure of gas exiting the cuvette is greater than that entering the cuvette, the flow rate of vented gas is greater than if the input and output gases had equal pressures.

The sample gas stream entering the analyzer is at atmospheric pressure (100 000 Pa), the proportion of $O_2$ in this gas being the same as the proportion exiting the cuvette i.e 19 990 parts in 100 010. The $pO_2$ of the gas entering the analyzer would therefore be 19988 Pa, and the $O_2$ analyzer would measure an apparent $O_2$ depletion of 12 Pa even though the cell depleted the supplied gas mixture by only 10 Pa. The rate of $O_2$ consumption estimated from this measurement would exceed the actual rate by 20%, and the estimated RQ value would be 1.67 compared to the actual value of 2.0.

EXAMPLE 2

Measurement of $O_2$ consumption by an organism having a respiratory quotient of 0.2.

Assume that gas at an atmospheric pressure of 100 kPa, containing 20 kPa $0_2$ in a balance of $N_2$ is supplied to a cuvette at 500 mL/min containing an organism which depletes the supplied $pO_2$ by 10 Pa. At an RQ of 0.2, the cell would add 0.2 kPa of $CO_2$ to the supplied gas for every 1 Pa of $O_2$ consumed. Therefore, the gas exiting the cuvette 6 (FIG. 1) would have a total pressure of 99992 Pa, containing 19 990 Pa $O_2$, 2 Pa $CO_2$ and 80 000 Pa $N_2$. The majority of gas exiting the cuvette is vented to atmosphere via vent 7, and since the total pressure of gas exiting the cuvette is lower than that entering the cuvette, the flow rate of vented gas is less than if the input and output gases had equal pressures.

The sample gas stream entering the analyzer is at atmospheric pressure (100 kPa), the proportion of $O_2$ in this gas being the same as the proportion exiting the cuvette i.e 19 990 parts in 99 992. The $pO_2$ of the gas entering the analyzer would therefore be 19 991 and the sample $O_2$ sensor would measure an apparent $O_2$ depletion of 9 Pa $O_2$ though the cell depleted the supplied gas mixture by 10 Pa. The rate of $O_2$ consumption estimated from this measurement would therefore be 90% of the actual rate, and the estimated RQ value would be 0.22 compared to the actual value of 0.20.

The type of errors caused by the occurrence of RQ values different from 1.0, as illustrated by the above examples, would also occur in estimating rates of $O_2$ consumption by photosynthetic cells with photosynthetic quotients different from 1.0.

To correct for the errors illustrated in examples 1 and 2 above, the amount of $CO_2$ produced or consumed by the organism, tissue or cells within the cuvette must be measured simultaneously with measurements of differential $O_2$. This may be achieved by incorporating a differential $CO_2$ analyzer into the gas exchange system in parallel with the differential $O_2$ analyzer as shown in FIG. 1. Output from the differential $CO_2$ analyzer may be read by the differential oxygen analyzer which then calculates a measured RQ or PQ value. The software of the differential $O_2$ analyzer incorporates the mathematical relationships between measured and actual respiratory and photosynthetic quotients, and these are used to correct for errors in measured $O_2$ differentials.

Figure 6:
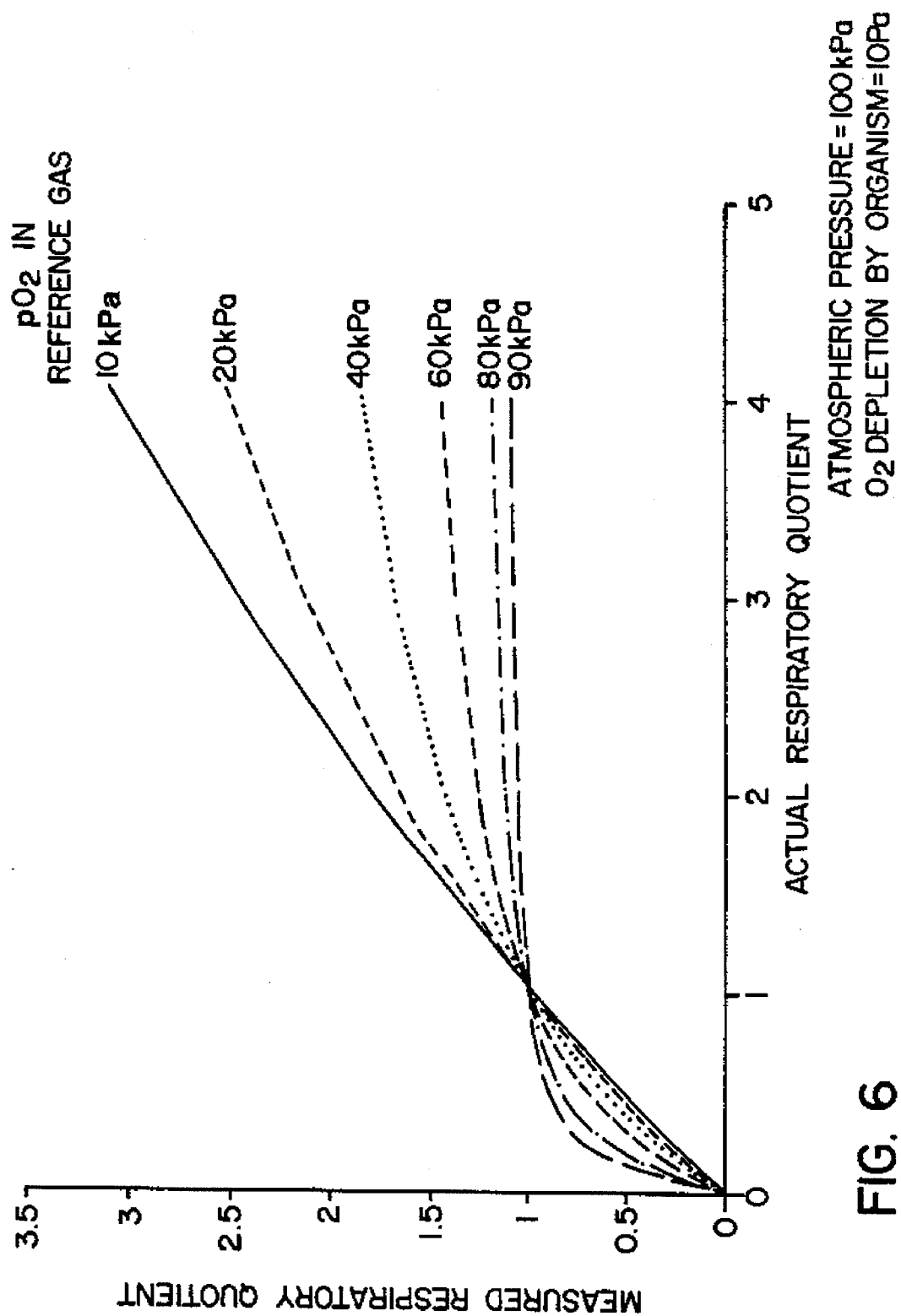
FIG. 6 shows the mathematical relationship between the actual respiratory quotient of an organism and the respiratory quotient measured from the outputs of the differential $O_2$ analyzer and a differential $CO_2$ analyzer, when various $pO_2$ are supplied to the cuvette containing the organism and the organism depletes this $pO_2$ by 10 kPa.

FIG. 6 shows the relationship between measured and actual respiratory quotient at various $pO_2$ in the gas supplied to the organism in the cuvette when the organism is depleting 10 Pa $O_2$ from this gas stream. An identical relationship occurs between values of measured and actual PQ when a photosynthetic organism is adding 10 Pa to the sample gas stream passing through the cuvette. The amount of $O_2$ added or removed from the sample gas stream affects these relationships, but the maximum difference that occurs between values measured at a $pO_2$ differential of 1 Pa and those measured at a $pO_2$ differential of 500 Pa is only 1.2%. Since the differential oxygen analyzer is designed predominantly for measuring very low (below 500 Pa) $O_2$ differentials, the error involved in assuming no effect of $O_2$ differential magnitude on the relationship between actual and measured respiratory and photosynthetic quotients is negligible.

Figure 7:
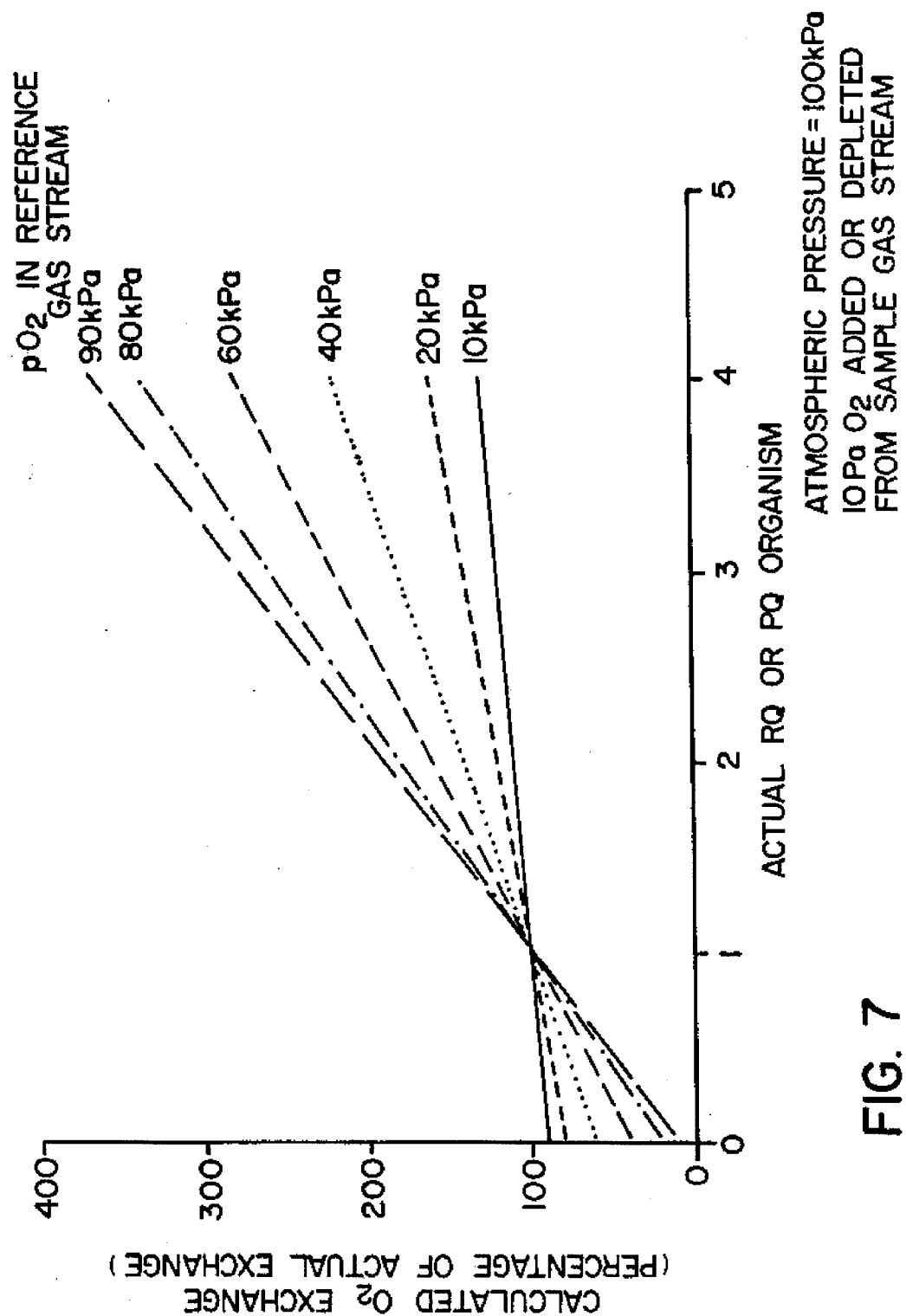
FIG. 7 shows the relationship between the actual respiratory or photosynthetic quotient of an organism and the extent to which the $O_2$ exchange in the sample gas stream measured by the differential $O_2$ analyzer underestimates or overestimates the $O_2$ exchange carried out by the organism.

The relationship illustrated in FIG. 6 allows actual RQ or PQ values to be determined from measured RQ and PQ values. The analyzer software uses these actual RQ and PQ values to calculate the extent to which the measured $O_2$ differential overestimates or underestimates the actual $O_2$ differential between the $pO_2$ in the reference gas stream and in the sample gas stream exiting from the cuvette. The relationship between the measured and actual $O_2$ differentials with respect to RQ and PQ at different $pO_2$ in the supplied gas stream is shown in FIG. 7. This figure shows the relationship between these parameters for an actual $O_2$ differential of 10 Pa between the reference and sample gas streams. However, the changes that occur in this relationship as $O_2$ differentials are increased between 1 and 500 Pa are negligible.

Use of a Double Differential Oxygen Analyzer for Simultaneous Measurement of Differential $pO_2$ and Differential $pCO_2$.

Figure 8:
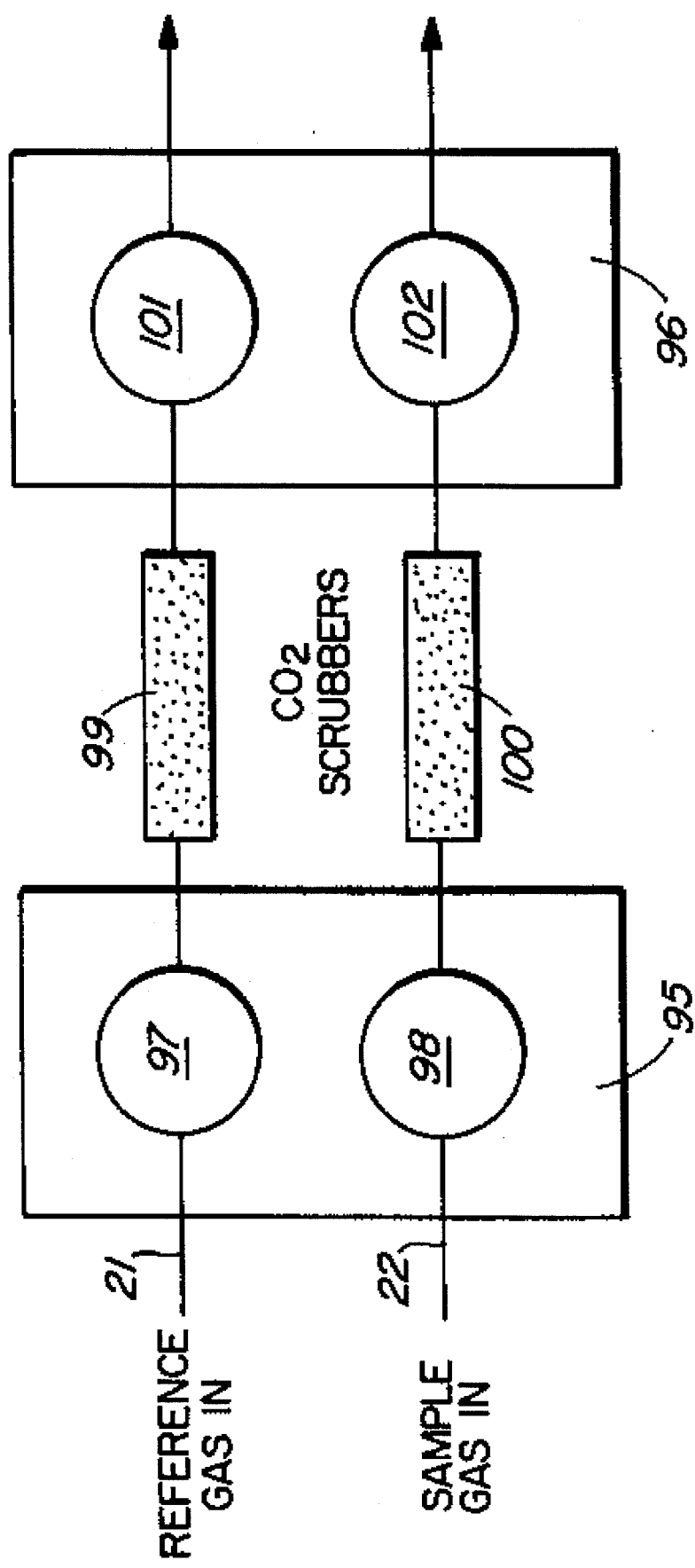
FIG. 8 shows the arrangement of $O_2$ sensors in a double differential $O_2$ analyzer designed for the simultaneous measurement of $O_2$ and $CO_2$ exchange.

An alternative embodiment of the differential $O_2$ analyzer described above may be used to measure differential $pO_2$ and differential $pCO_2$ simultaneously in the same instrument. A schematic of such an instrument is shown in FIG. 8. The instrument has the same general design as that shown in FIG. 2, except that it incorporates two sensor blocks 95 and 96 each containing a reference and sample $O_2$ sensor configured in differential mode. The reference (21) and sample (22) gases pass through the reference (97) and sample (98) $O_2$ sensors, respectively, in the first block, and on exiting the sensors are scrubbed of any $CO_2$ they may contain by passage through columns (99 and 100) containing soda lime or similar $CO_2$ absorbing material. The scrubbed reference and sample gases then enter the second sensor block 96 and pass through the second reference (101) and sample (102) $O_2$ sensors, respectively.

The removal of $CO_2$ between the first and second sensor housings causes the $pO_2$ of the reference and sample gases to increase so that the differential $pO_2$ measured between the $O_2$ sensors in the first housing differs from the differential $pO_2$ measured between the $O_2$ sensors in the second housing. For example, consider a situation in which an organism with a RQ of 2.0 is supplied with a gas stream containing 20 000 Pa $O_2$, 50 Pa $CO_2$ and 79 950 N2 at an atmospheric pressure of 100 kPa. If the organism's respiratory activity depletes the supplied $pO_2$ by 10 Pa, the gas exiting the cuvette will contain 19 990 Pa $O_2$, 70 Pa $CO_2$ and 79 950 N2. However, since the gas is vented to atmosphere (at a pressure of 100 kPa), the composition of gas entering the first sample $O_2$ sensor will be 19 988 Pa $0_2$, 70 Pa $CO_2$ and 79 942 Pa N2, and the differential $pO_2$ between the sample and reference $O_2$ sensor will be 12 Pa $O_2$. After $CO_2$ is scrubbed from the sample gas stream, the proportion of $O_2$ in the sample gas will rise from 19 988/100 000 to 19 988/99 930, and the $pO_2$ of the sample gas will increase to 20002 Pa. After $CO_2$ is scrubbed from the reference gas the proportion of $O_2$ in the gas will rise from 20 000/100 000 to 20 000/99 950, and the $pO_2$ in the reference gas will increase to 20 0010 Pa. Therefore, the $O_2$ differential between the $O_2$ sensors in the second housing will be 8 Pa, and the ratio of the first differential sensor output to the second differential sensor output will be 12/8=1.5

Figure 9:
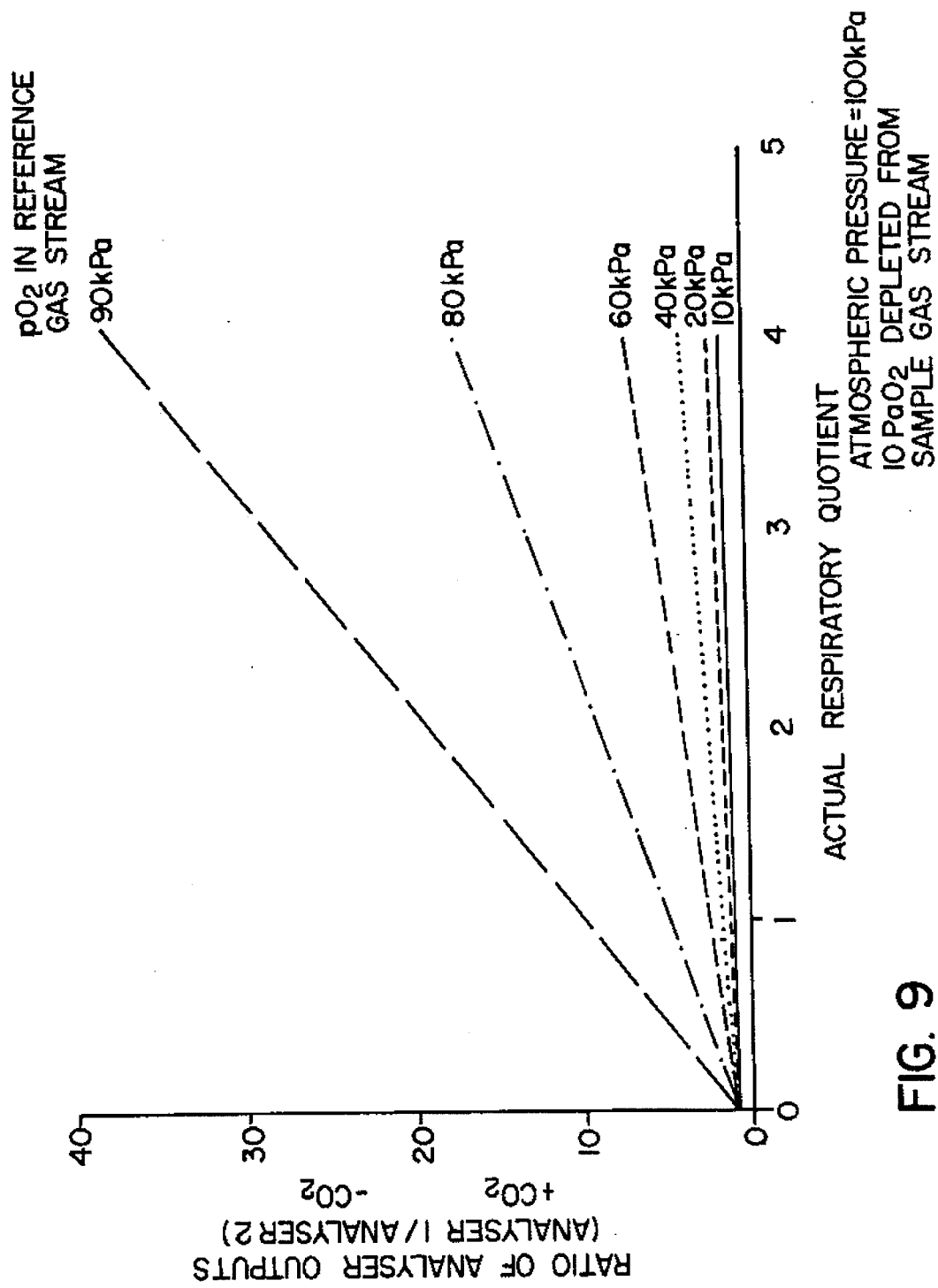
FIG. 9 shows the relationship between the ratio of the sensor outputs in the double differential $O_2$ sensor and the actual respiratory quotient of an organism when the organism is supplied with 50 Pa $CO_2$ at various $pO_2$ in the sample gas stream and depletes this stream by 10 Pa $O_2$.

The ratio of the outputs of the two differential sensors depends on the actual RQ or PQ of the organism, tissue or cells in the cuvette, and the $pO_2$ and $pCO_2$ of the gas supplied to the cuvette. The extent to which the biological sample changes the $pO_2$ of the supplied gas also has an effect on the ratio, but this is negligible over the range of $O_2$ differentials that the instrument is designed to measure. FIG. 9 shows an example of the relationship among the ratio of the sensor outputs, the actual RQ of the biological sample and the $pO_2$ in the supplied gas stream when 50 Pa $CO_2$ is present in the supplied gas and the sample depletes the $pO_2$ in the sample gas stream by 10 Pa $O_2$. A similar relationship exists between the ratio of the sensor outputs and the actual PQ of a photosynthetic organism when this organism is supplied with gases of similar composition and adds 10 Pa $O_2$ to the sample gas stream. The software of the double differential analyzer incorporates the relationships between these parameters at various supplied $pO_2$ and $pCO_2$, and is therefore able to calculate the actual RQ or PQ of the biological material in the cuvette from the ratio of the differential sensor outputs. Having calculated the actual RQ or PQ, the extent to which the $O_2$ differential measured by the first differential sensor over or underestimates the $O_2$ uptake or production by the material in the cuvette can be calculated in software using the relationship shown in FIGS. 7. From this, the true $O_2$ uptake or production by the material in the cuvette is calculated, and the RQ or PQ determined from the ratio of the outputs of the two differential sensors in the instrument is used to calculate uptake or production of $CO_2$. The double differential $O_2$ analyzer therefore provides simultaneous measurements of $O_2$ depletion or production, $CO_2$ depletion or production and measurements of RQ or PQ.

It should be noted that alternative embodiments of the double differential $O_2$ analyzer shown in FIG. 8 may be used to measure the uptake or production rate of any gas that is produced or consumed by an organism, tissue or cell that is also producing or consuming $O_2$. The instrument need only be modified by changing the $CO_2$ scrubbers between the two sensor housings for scrubbers which remove the gas in question. Removal of this gas by the scrubbers will have the same effect as removing $CO_2$ i.e. there will be a change in the differential $pO_2$ between the reference and sample gas streams after the gas is scrubbed. The ratio of the differential $O_2$ sensor outputs can then be used to calculate the ratio of $O_2$ exchange to the ratio of exchange of the other gas (equivalent to RQ and PQ), and this ratio can then be used to calculate both actual $O_2$ exchange and exchange of the other gas in the same manner as that described for measurement of $CO_2$ exchange described above.

We claim:

1. An apparatus for measuring differential oxygen concentrations in two flowing gas streams comprising:

means to control pressure and flow rate of said gas streams;

means within said temperature-controlled housing means to generate signals representative of pressure and oxygen concentration differentials between said gas streams, comprising first and second oxygen sensors, connected in parallel with each other with opposite polarity, and wherein said first sensor is connected in series with a fixed resistance and said second sensor is connected in series with at least a selected portion of said fixed resistance, such that, at a selected oxygen concentration in both said sensors, the voltage drop across the fixed resistance is zero;

and computer means to monitor said pressure, flow rate and temperature and said signals representative of said differential pressure and oxygen concentration so as to measure and record differential oxygen concentration in said gas streams.

2. An apparatus as claimed in claim 1 wherein said first and second oxygen sensors have lower and higher current outputs respectively at a given oxygen concentration.

3. An apparatus as claimed in claim 2 including means to amplify said signal representative of the differential oxygen concentration.

4. An apparatus as claimed in claim 3 wherein said means to amplify said signal comprises a chopper amplifier in series with a low pass filter.

5. An apparatus as claimed in claim 4 wherein said low pass filter is in the range 0.5–5.0 Hz.

6. An apparatus as claimed in claim 2 including means to calibrate said apparatus comprising means to control the pressure differential between the gas streams the oxygen concentrations of which are monitored by said first and second oxygen sensors.

7. An apparatus as claimed in claim 2 including means to measure the pressure differential between the gas streams the oxygen concentrations of which are monitored by said first and second oxygen sensors.

8. An apparatus as claimed in claim 1 wherein said first gas flow path contains a reference oxygen bearing gas and said second gas flow path contains a sample oxygen bearing gas.

9. An apparatus as claimed in claim 8 including means to bypass at least a portion of said reference gas and said sample gas from a respective said flow path, upstream of said means to introduce said gas streams.

10. An apparatus as claimed in claim 9 including means to heat and control temperature of said oxygen sensor means.

11. An apparatus as claimed in claim 10 including pressure sensor means to monitor atmospheric pressure.

12. An apparatus as claimed in claim 9 wherein said means to introduce said gas streams is a pump means.

13. Apparatus as claimed in claim 1 including means to measure absolute oxygen concentration in one of said gas streams.

14. An apparatus for measuring differential concentrations of two different gases contained in two flowing gas streams comprising a first apparatus as claimed in claim 1 connected in series to a second apparatus as claimed in claim 1, with a pair of scrubbers operatively connected there between so as to remove one of said two gases from the two flowing gas streams.

15. An apparatus as claimed in claim 14 wherein said one of said two gases is carbon dioxide and said scrubbers are soda-lime scrubbers.

* * * * *

UNITED STATES PATENT AND TRADEMARK OFFICE
CERTIFICATE OF CORRECTION

PATENT NO.: 5,542,284
DATED: August 6, 1996
INVENTORS: David B. Layzell, Stephen Hunt, and Adrian N. Dowling It is certified that error appears in the above-identified patent and that said Letters Patent is hereby corrected as shown below:

In the claims, at column 17, lines 25 to 45, claim 1 should read:

1. An apparatus for measuring differential oxygen concentrations in two flowing gas streams comprising:

means to control pressure and flow rate of said gas streams;

means to introduce said gas streams into a temperature-controlled housing means having first and second gas flow paths therethrough for passage of respective ones of said gas streams;

means within said temperature-controlled housing means to generate signals representative of pressure and oxygen concentration differentials between said gas streams, comprising first and second oxygen sensors, connected in parallel with each other with opposite polarity, and wherein said first sensor is connected in series with a fixed resistance and said second sensor is connected in series with at least a selected portion of said fixed resistance, such that, at a selected oxygen concentration in both said sensors, the voltage drop across the fixed resistance is zero;

and computer means to monitor said pressure, flow rate and temperature and said signals representative of said differential pressure and oxygen concentration so as to measure and record differential oxygen concentration in said gas streams.

Signed and Sealed this

Fourth Day of August, 1998

*Attest:*

BRUCE LEHMAN

*Attesting Officer*  *Commissioner of Patents and Trademarks*